United States Patent
Harrigan

[19]

[11] Patent Number: 5,957,812
[45] Date of Patent: Sep. 28, 1999

[54] MAXIMUM CONTRACTION UNIT

[76] Inventor: Tracy J. Harrigan, 8 Arbour St., West Islip, N.Y. 11795

[21] Appl. No.: 08/779,228

[22] Filed: Jan. 1, 1997

[51] Int. Cl.⁶ .................................................... A63B 69/00
[52] U.S. Cl. ................................. 482/8; 482/1; 482/900; 601/23
[58] Field of Search ............................... 482/1–9, 48, 83, 482/92, 148, 900–902, 114, 115; 601/23

[56] References Cited

U.S. PATENT DOCUMENTS

| | | | |
|---|---|---|---|
| 4,208,048 | 6/1980 | Winterbottom | 482/84 |
| 5,713,370 | 2/1998 | Cook | 482/114 |
| 5,733,193 | 3/1998 | Allard et al. | 463/7 |

*Primary Examiner*—Glenn Richman
*Attorney, Agent, or Firm*—Michael I. Kroll

[57] ABSTRACT

A maximum contraction unit (10) comprising a cabinet (12) having a front panel (14), a pair of side panels (16), a top panel (18), a bottom panel (20) and a rear panel (22) hinged at (24) to one of the side panels (16), to gain access to the interior of the cabinet (12). A structure (26) is for keeping the cabinet (12) in an upright position. A facility (28) in the cabinet (12) is for producing electronic impulses. A component (30) on the front panel (14) of the cabinet (12) is for activating the electronic impulses producing facility (28) by the insertion of paper money. An assembly (32) is for carrying the electronic impulses from the electronic impulses producing facility (28) to muscles in a body of a person (34), so as to stimulate the muscles to contract and exercise.

11 Claims, 6 Drawing Sheets

MAXIMUM CONTRACTION UNIT

BACKGROUND OF THE INVENTION

FIELD OF THE INVENTION

When a person performs an exercise, the brain sends a message down the spinal cord through nerves innervating all the muscles that the person is using to cause the muscles to contract. This is referred to a voluntary muscle action, so that in essence the brain controls the muscles.

The idea behind electrical muscle stimulation (EMS) is that an outside electrical source stimulates the nerves to send these signals to the muscles to contract. This is accomplished by passing low electrical current through electrode pads placed over the muscles. The current passes through the skin to the nerves in the immediate area, stimulating the connecting muscles to contract.

The instant invention relates generally to electronic muscle exercise devices and more specifically it relates to a maximum contraction unit. The maximum contraction unit is a vending machine which allows a person to control the amount of electronic impulses and time needed to receive the electrical impulses, to stimulate the muscles to contract and exercise.

DESCRIPTION OF THE PRIOR ART

Numerous electronic muscle exercise devices have been provided in prior art that are adapted to produce muscle stimulation by electronic treatment, in which very weak electronic impulses are applied through electrode pads into the skin to motor points that causes muscles to contract and exercise, which is similar to the muscles receiving signals from the brain. While these units may be suitable for the particular purpose to which they address, they would not be as suitable for the purposes of the present invention as heretofore described.

SUMMARY OF THE INVENTION

A primary object of the present invention is to provide a maximum contraction unit that will overcome the shortcomings of the prior art devices.

Another object is to provide a maximum contraction unit that is a vending machine, in which a person can connect electrode pads to various parts of the body and control the amount of electronic impulses and time needed to stimulate the muscles to contract and exercise.

An additional object is to provide a maximum contraction unit in which the vending machine can be placed within a gym, so that people coming to the gym can deposit various amounts of paper money into a slot within a bill acceptor, to determine the length of time to operate an electronic muscle exercise unit built therein.

A further object is to provide a maximum contraction unit that is simple and easy to use.

A still further object is to provide a maximum contraction unit that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein.

Similar reference characters denote corresponding features consistently throughout the attached drawings.

DETAILED DESCRIPTION OF THE PREFERRED EMBODIMENTS

Figure 1:
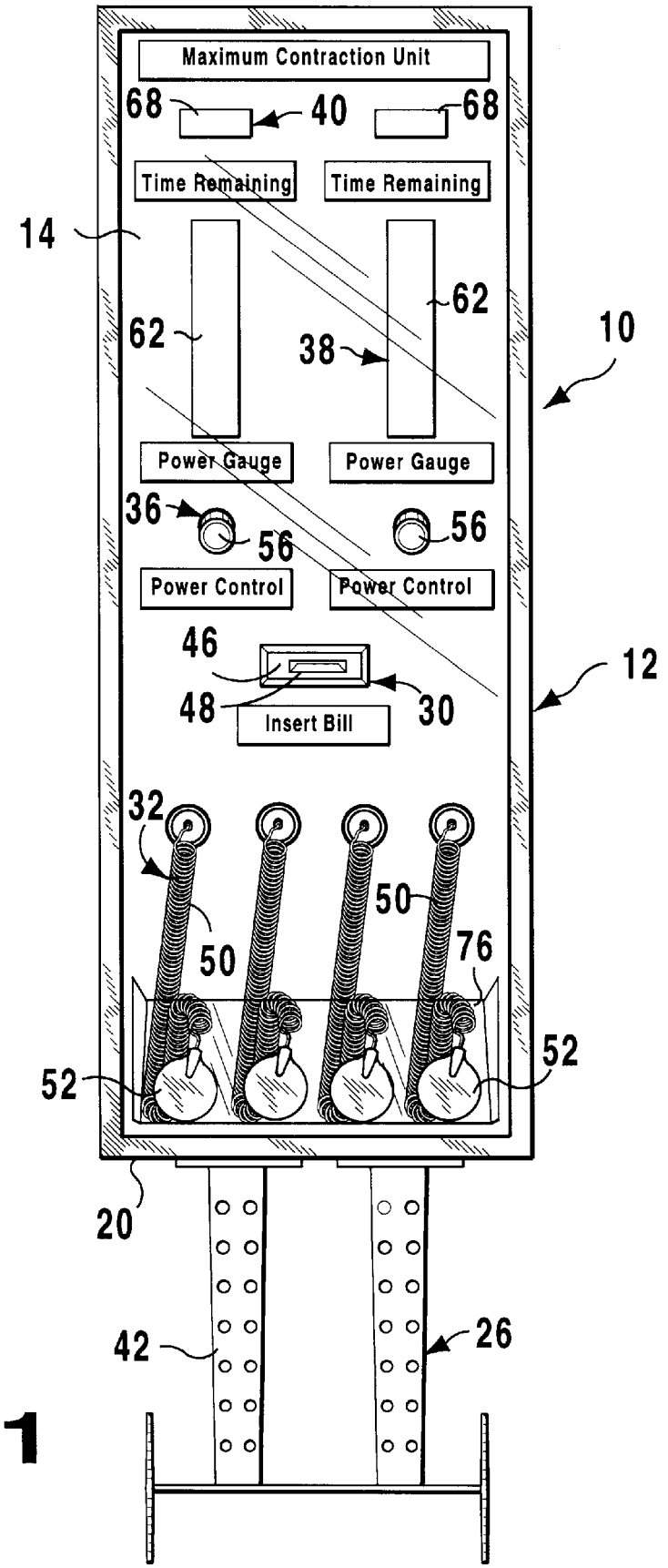
FIG. 1 is a front elevational view of the instant invention.

Turning now descriptively to the drawings, in which similar reference characters denote similar elements throughout the several views, FIGS. 1 to 5 illustrate a maximum contraction unit 10 comprising a cabinet 12 having a front panel 14, a pair of side panels 16, a top panel 18, a bottom panel 20 and a rear panel 22, hinged at 24 to one of the side panels 16 to gain access to the interior of the cabinet 12. A structure 26 is for keeping the cabinet 12 in an upright position. A facility 28 in the cabinet 12 is for producing electronic impulses. A component 30 on the front panel 14 of the cabinet 12 is for activating the electronic impulses producing facility 28 by the insertion of paper money. An assembly 32 is for carrying the electronic impulses from the electronic impulses producing facility 28 to muscles in a body of a person 34, so as to stimulate the muscles to contract and exercise.

Equipment 36 is for manually controlling the power output of the electronic impulses producing facility 28. Paraphernalia 38 is for displaying the power output from the manually controlling equipment 36 on the front panel 14 of the cabinet 12. An assemblage 40 for indicating time remaining for operation of the electronic impulses producing facility 28 is on the front panel 14 of the cabinet 12.

The upright position keeping structure 26 is a stand 42 affixed to the bottom panel 20 of the cabinet 12. The stand 42 can sit upon a floor and support the cabinet 12 in its upright position. The electronic impulses producing facility 28 is an electrical muscle stimulation unit (EMS) 44. The activating component 30 is a bill acceptor cash box with a sensor 46, having a slot 48 to receive paper money inserted therein.

Figure 3:
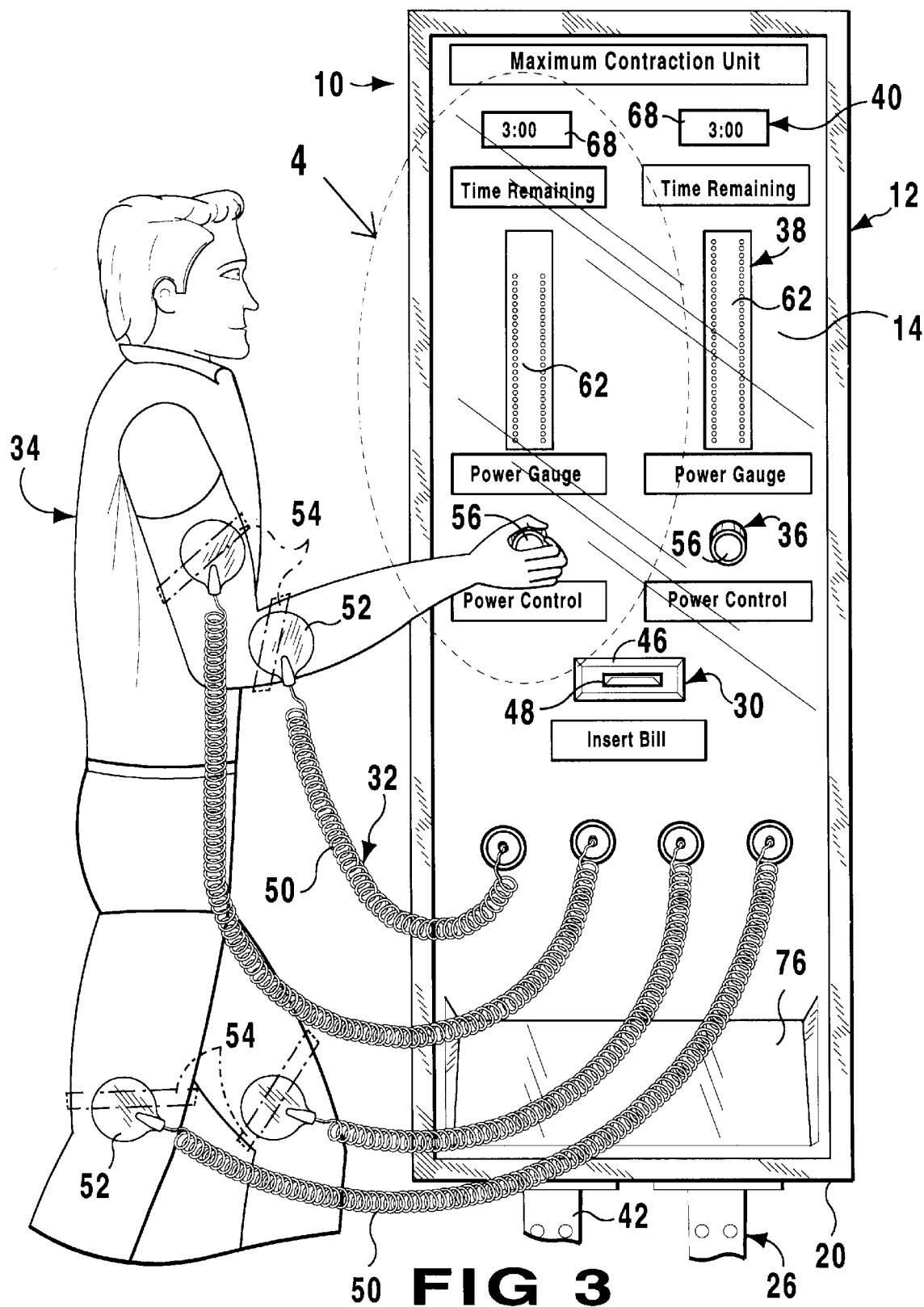
FIG. 3 is a front elevational view similar to FIG. 1 with parts broken away, showing a person operating same.
Figure 4:
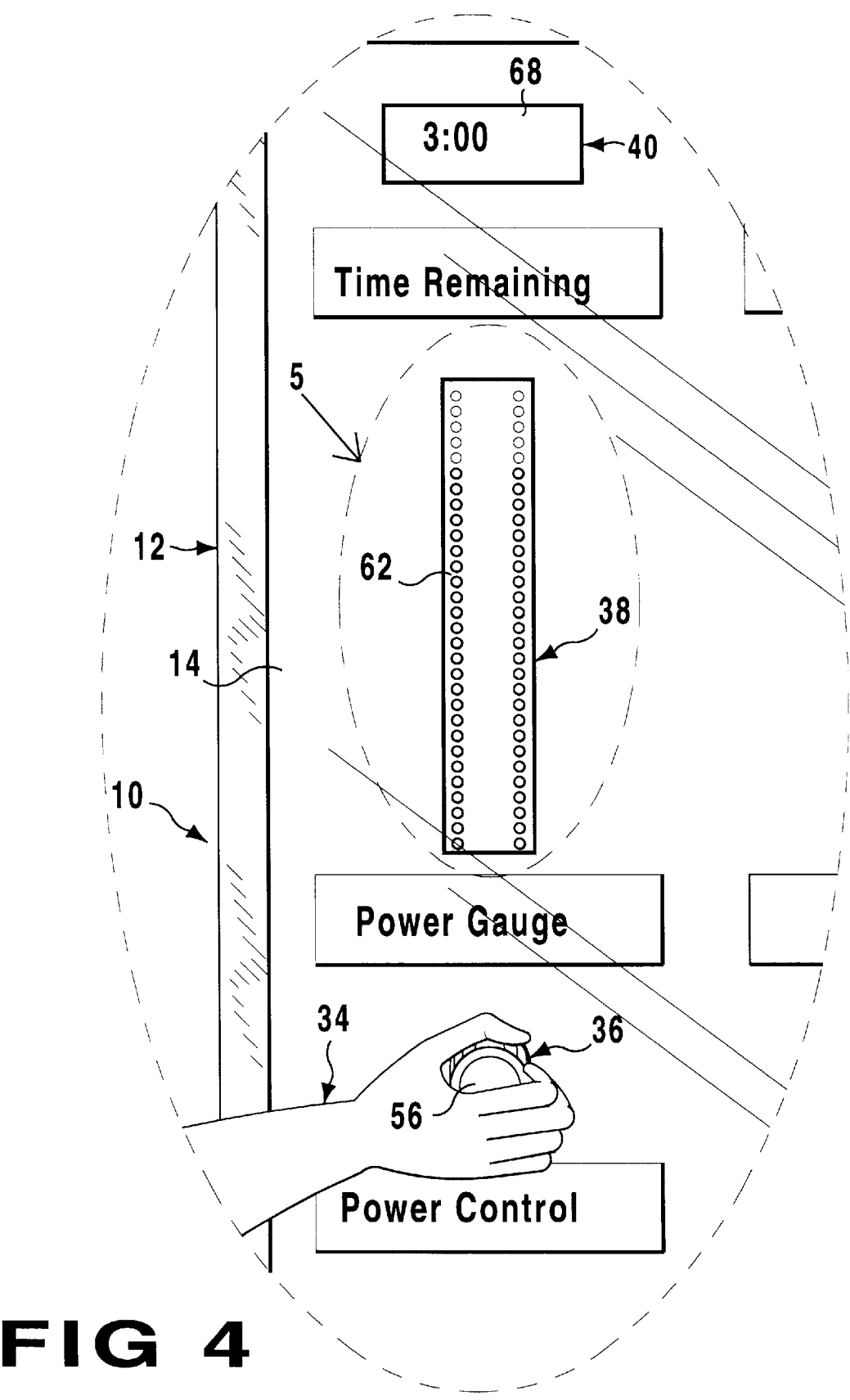
FIG. 4 is an enlarged front elevational view of an area indicated by arrow 4 in FIG. 3.
Figure 5:
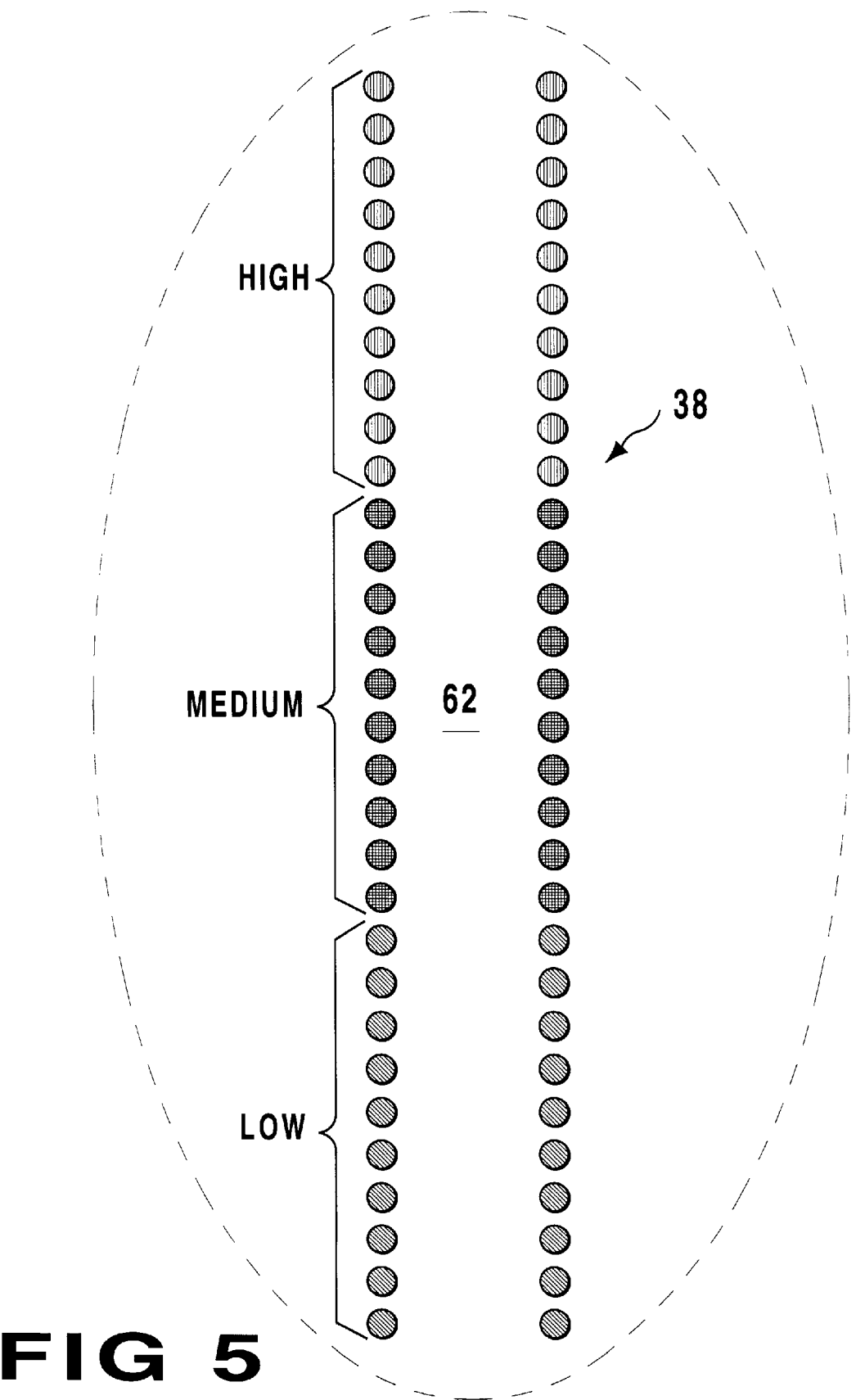
FIG. 5 is a further enlarged elevational view of an area indicated by arrow 5 in FIG. 4, showing the various stages of one of the power gauge displays in greater detail.

The electronic impulses carrying assembly 32 includes a plurality of electronic wires 50 mounted on the front panel 14 of the cabinet 12 and are electrically connected to the electronic impulses producing facility 28. A plurality of electrode pads 52 are provided. Each electrode pad 52 is electrically connected to one of the electronic wires 50. Two of the electrode pads 52 can be placed upon the skin of the person 34 at the muscles to be stimulated. A plurality of VELCRO straps 54, shown in phantom in FIG. 3, is to retain the electrode pads 52 upon the skin of the person 34.

The manually controlling equipment 36 consists of a plurality of power control knobs 56 rotatively mounted on the front panel 14 of the cabinet 12. A plurality of continuous belts 58 are provided. Each belt 58 extends from one knob 56 to the electronic impulses producing facility 28. The power output displaying paraphernalia 38 is a plurality of power gauges 60 with display screens 62 mounted in the front panel 14 of the cabinet 12. The person 34 can see low, medium and high color coded settings made by the manually controlling equipment 36.

Figure 2:
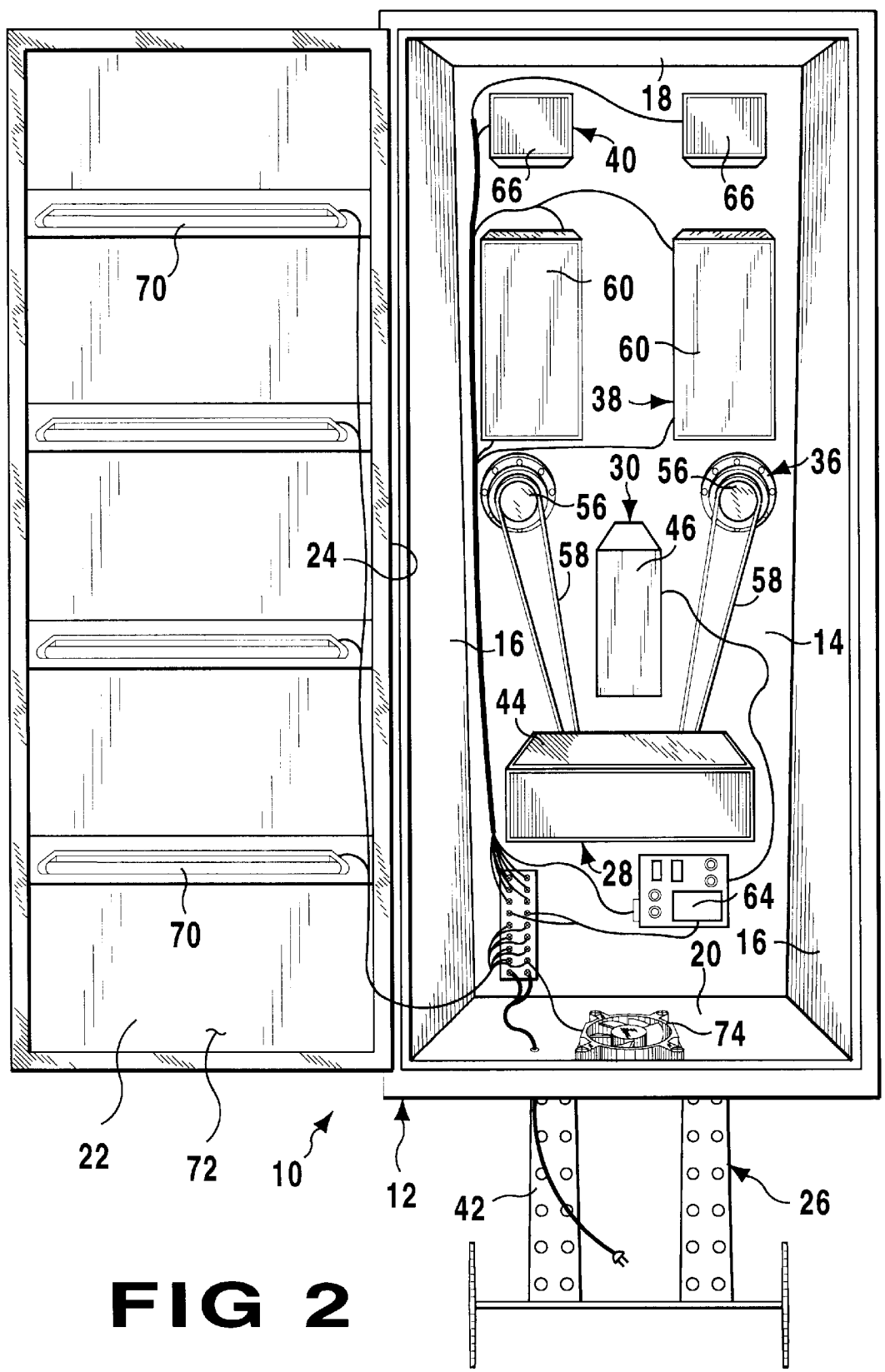
FIG. 2 is a rear elevational view thereof, with the back panel opened to see the various components therein.

The time remaining indicating assemblage 40 comprises a timer circuit 64 carried within the cabinet 12. A plurality of time clocks 66 with time display faces 68 are mounted in the front panel 14 of the cabinet 12, so that the person 34 can see the time remaining. A plurality of lamps 70, as shown in FIG. 2, are mounted onto an interior surface 72 of the rear panel 22 of the cabinet 12, to illuminate the power output displaying paraphernalia 38 and time remaining indicating assemblage 40.

A fan 74 is mounted onto the bottom panel 20 of the cabinet 12, to keep the interior of the cabinet 12 cool. A holder 76 is affixed to the front panel 14 of the cabinet 12 adjacent the bottom panel 20, so as to store the electrode pads 52 therein when not in use.

OPERATION OF THE INVENTION

Figure 6:
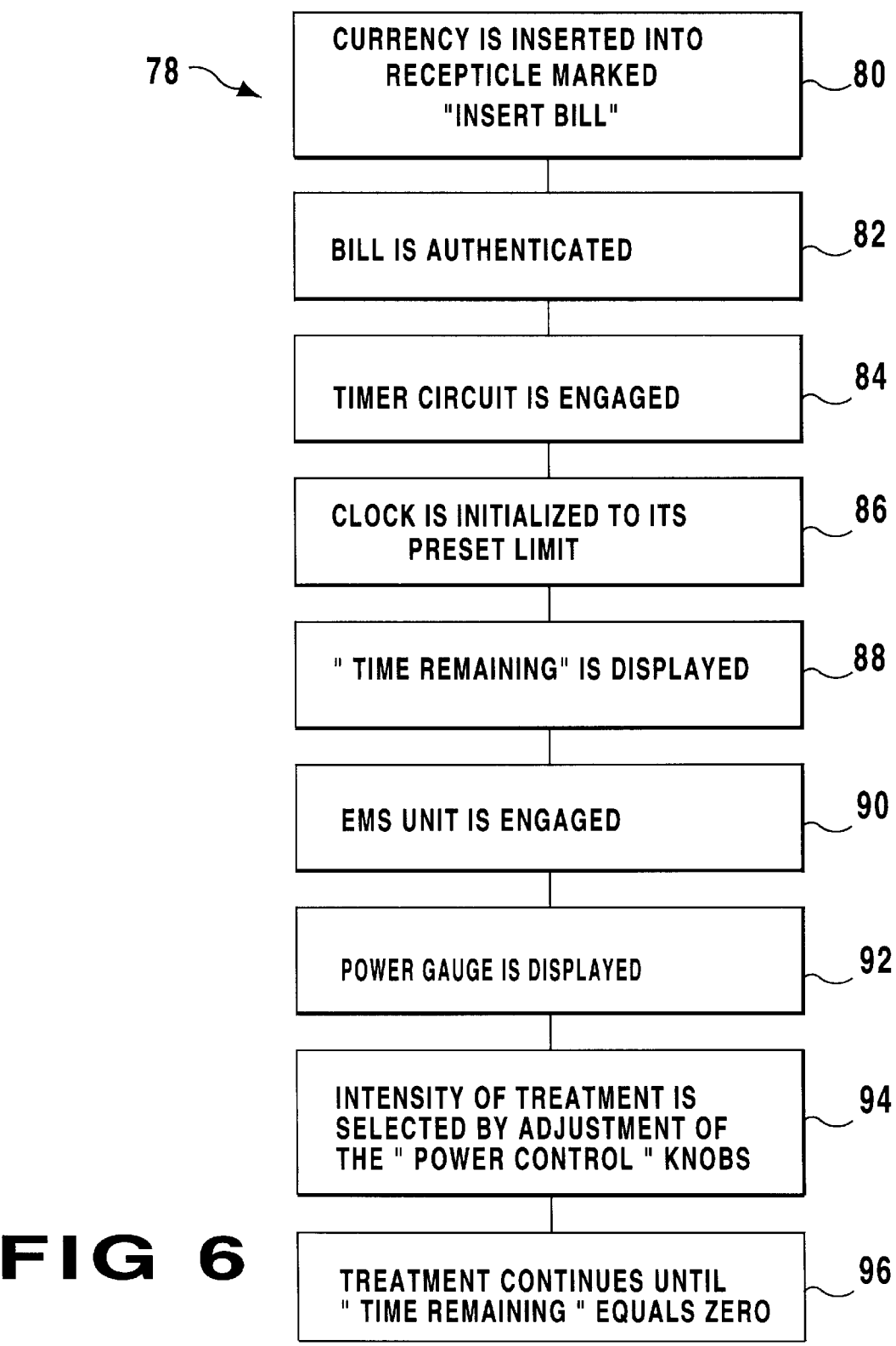
FIG. 6 is a block diagram flow chart, showing how to operate the instant invention.

FIG. 6 shows a block diagram flow chart 78. The flow chart 78 explains how to operate the maximum contraction unit 10 properly and safely and reads as follows:

1. First box 80:
   Currency is inserted into receptacle marked "Insert Bill".
2. Second box 82:
   Bill is authenticated.
3. Third box 84:
   Timer circuit is engaged.
4. Fourth box 86:
   Clock is initialized to its preset limit.
5. Fifth box 88:
   "Time Remaining" is displayed.
6. Sixth box 90:
   EMS unit is engaged.
7. Seventh box 92:
   Power gauge is displayed.
8. Eighth box 94:
   Intensity of treatment is selected by adjustment of the "Power Control" knobs.
9. Ninth box 96:
   Treatment continues until "Time Remaining" equals zero.

LIST OF REFERENCE NUMBERS

10 maximum contraction unit
12 cabinet of 10
14 front panel of 12
16 side panel of 12
18 top panel of 12
20 bottom panel of 12
22 rear panel of 12
24 hinge between 16 and 22
26 upright position keeping structure of 10
28 electronic impulses producing facility of 10
30 activating component of 10
32 electronic impulses carrying assembly of 10
34 person
36 manually controlling equipment of 10
38 power output displaying paraphernalia of 10
40 time remaining indicating assemblage of 10
42 stand for 26
44 electrical muscle stimulation unit for 28
46 bill acceptor cash box with sensor for 30
48 slot in 46
50 electronic wire of 32
52 electrode pad of 32
54 VELCRO straps for 52
56 power control knob of 36
58 continuous belt of 36 between 28 and 56
60 power gauge of 38
62 display screen of 60
64 timer circuit of 40
66 time clock of 40
68 time display face of 66
70 lamp on 72
72 interior surface of 22
74 fan on 20
76 holder on 14 for 52
78 flow chart for 10
80 first box of 78
82 second box of 78
84 third box of 78
86 fourth box of 78
88 fifth box of 78
90 sixth box of 78
92 seventh box of 78
94 eighth box of 78
96 ninth box of 78

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A maximum contraction vending unit comprising:
   a) a cabinet having a front panel, a pair of side panels, a top panel, a bottom panel and a rear panel hinged to one of said side panels to gain access to the interior of said cabinet;
   b) means for keeping said cabinet in an upright position;
   c) means in said cabinet for producing electronic impulses comprising an electrical muscle stimulation unit;
   d) means on said front panel of said cabinet for activating said electronic impulses producing means by the insertion of paper money;
   e) means for carrying the electronic impulses from said electrical muscle stimulating unit to selected muscles in a body of a person comprising a plurality of electrical wires mounted on said front panel of said cabinet electrically connected to said electrical muscle stimulating unit and an electrode pad connected to each of said electrical wires for attaching to selected locations on the skin of said person in suitable locations for stimulating selected muscles to contract and exercise; and f) means on said front panel for manually controlling the power output of said electrical muscle stimulating unit and means for displaying said power output comprising display screens for showing low, medium and high color coded settings for said electrical muscle stimulating unit.

2. A maximum contraction unit as recited in claim 1, further including means for indicating time remaining for operation of said electronic impulses producing means on said front panel of said cabinet.

3. A maximum contraction unit as recited in 1, wherein said upright position keeping means is a stand affixed to said bottom panel of said cabinet, so that said stand can sit upon a floor and support said cabinet in its upright position.

4. A maximum contraction unit as recited in claim 1, wherein said activating means is a bill acceptor cash box with sensor having a slot to receive paper money inserted therein.

5. A maximum contraction unit as recited in claim 1, further including a plurality of loop and hook straps to retain said electrode pads upon the skin of the person.

6. A maximum contraction unit as recited in claim 1, wherein said manually controlling means includes:

a) a plurality of power control knobs rotatively mounted on said front panel of said cabinet; and b) a plurality of continuous belts, wherein each said belt extends from one said knob to said electronic impulses producing means.

7. A maximum contraction unit as recited in claim 2, wherein said time remaining indicating means includes:

a) a timer circuit carried within said cabinet; and b) a plurality of time clocks with time display faces mounted in said front panel of said cabinet, so that the person can see the time remaining.

8. A maximum contraction unit as recited in claim 2, further including a plurality of lamps mounted onto an interior surface of said rear panel of said cabinet to illuminate said power output displaying means and said time remaining indicating means.

9. A maximum contraction unit as recited in claim 8, further including a fan mounted onto said bottom panel of said cabinet to keep the interior of said cabinet cool.

10. A maximum contraction unit as recited in claim 1, further including a holder affixed to said front panel of said cabinet adjacent said bottom panel, so as to store said electrode pads therein when not in use.

11. The method of vending electrical muscle stimulation comprising the steps of:

a) inserting currency in a vending machine comprising a cabinet containing an electrical muscle stimulation unit, a plurality of electrical wires electrically connected to said electrical muscle stimulating unit, and an electrode pad connected to each of said electrical wires to activate said electrical muscle stimulation unit and engage a timer circuit to preset a limit;

b) attaching said pads to selected locations on the skin of a person in suitable locations for stimulating selected muscles to contract and exercise;

c) adjusting dials on said cabinet to set a power level for intensity of treatment and displaying the power level using color coded markers on a screen; and d) permitting said treatment to continue until the preset limit expires.

* * * * *